United States Patent [19]
Teshima

[11] Patent Number: 6,083,759
[45] Date of Patent: Jul. 4, 2000

[54] BLOOD SMEARING CASSETTE

[75] Inventor: Dick Y. Teshima, Honolulu, Hi.

[73] Assignee: University of Hawaii, Honolulu, Hi.

[21] Appl. No.: 09/000,710

[22] Filed: Dec. 30, 1997

[51] Int. Cl.$^7$ .................................................. G02B 21/34
[52] U.S. Cl. ..................... 436/174; 118/100; 359/396; 422/99; 422/100; 422/103; 427/2.11; 435/288.3; 436/46; 436/180
[58] Field of Search ................................ 422/99, 100, 102, 422/103, 104; 359/396–398; 436/46, 174, 180; 435/288.3; 118/100; 427/2.11

[56] References Cited

U.S. PATENT DOCUMENTS

| | | |
|---|---|---|
| 1,858,308 | 5/1932 | Schiller . |
| 3,589,557 | 6/1971 | Johnson . |
| 3,683,850 | 8/1972 | Grabhorn . |
| 3,880,111 | 4/1975 | Levine et al. . |
| 4,319,542 | 3/1982 | Ojima et al. . |
| 4,407,843 | 10/1983 | Sasaki et al. . |
| 4,494,479 | 1/1985 | Drury et al. . |

FOREIGN PATENT DOCUMENTS

| | | |
|---|---|---|
| 439124 | 5/1925 | Germany . |

*Primary Examiner*—Jan Ludlow
*Attorney, Agent, or Firm*—James Creighton Wray; Meera P. Narasimhan

[57] ABSTRACT

The present invention is a blood smearing cassette that quickly, efficiently and reliably prepares peripheral blood smears. The cassette holds two glass slides, a spreader slide and a smear slide, at specific angles to each other. The blood smearing cassette allows untrained personnel to make consistent and proper blood smears. The user slips a smear slide into the smear slide receiver, and a spreader slide into the spreader slide receiver. A small amount of blood is placed on the smear slide, which is then pulled up to the spreader slide until the drop of blood is in contact with the spreader slide. The blood is allowed to spread across the bottom of the spreader slide. The smear slide is then pulled back out of the cassette, leaving a thin film of blood on the smear slide. The length and thickness of the film are controlled by varying the speed at which the smear slide is pulled and varying angles between the two slides. A mechanism may be used for connecting the spreader slide receiver to the smear slide receiver that allows various angles between the slides to be selected depending on the viscosity of the blood sample.

34 Claims, 5 Drawing Sheets

BLOOD SMEARING CASSETTE

BACKGROUND OF THE INVENTION

A peripheral blood smear is made by applying a small amount of blood onto a microscope slide. A second slide is used to smear the blood into a thin film. Much practice is needed to master that wedge technique. Improper smearing can cause morphological alterations in the cells, making microscopic appearance of cells misleading. Factors such as size of the blood drop, angle of the spreader slide, speed of smearing, steadiness of the hand holding the spreader slide and amount of pressure applied onto the blood drop affect the quality of the blood smear. Although smears were made by trained laboratorians in the past, those tasks are now delegated to less trained personnel as a result of recent changes in the health care delivery pattern. A need exists for eliminating the undesirable factors that affect the quality of blood smears.

SUMMARY OF THE INVENTION

Peripheral blood smears are currently made by manually applying a drop of blood onto a microscope slide. The blood is spread by using a second slide to smear the blood into a thin film. The blood smears are then examined to clinically diagnose hematological diseases. Deriving full value from blood smear examinations requires a well-prepared, well-stained blood smear.

The current invention quickly, efficiently and reliably prepares a blood smear. In a preferred embodiment, the cassette holds two glass slides, a smear slide and a spreader slide, at specific angles to each other allowing relatively untrained personnel to make consistent and proper blood smears.

To use the cassette, the operator preferably slips the smear slide into the opening of the cassette that positions the slide horizontally. The spreader slide is slipped into another opening at the top of the cassette. The spreader slide drops onto the middle of the smear slide by gravity and is preferably held at approximately a 30–40° angle. A small amount of blood is placed on the smear slide, and the horizontal smear slide is then pulled until the bottom of the spreader slide is in contact with the drop of blood. The blood is allowed to spread across the bottom of the spreader slide. The smear slide is then pulled back out of the cassette, leaving a thin film of blood on the smear slide. The length and thickness of the film is controlled by pulling the smear slide at different speeds.

The cassette allows less trained personnel to prepare proper blood smears. The cassette is also small, portable and lightweight, which allows it to be used outside of the clinical laboratory setting such as at an outpatient clinic or at a patient's bedside. The cassette allows for relatively untrained laboratory technicians, nurses and medical clerks to produce consistent and proper blood smears without much training. The amount of training time required for clinical personnel using the cassette to make proper and consistent blood smears is greatly reduced. The manual method of creating blood smears requires considerable dexterity and training, which is all but eliminated by the cassette. Allowing less trained personnel to prepare blood smears permits technologists and technicians to do more important tasks.

In another preferred embodiment, a mechanism is added that allows for adjustment of the angle between the spreader slide and the smear slide. The thicker the blood sample, the lower the angle that the spreader slide must be positioned in relation to the smear slide. The more liquid the blood sample, the higher the angle that the spreader slide must be positioned in relation to the smear slide. Different angles permit control of the film length and thickness according to sample viscosity (i.e., anemia vs. polycythemia).

These and further and other objects and features of the invention are apparent in the disclosure, which includes the above and ongoing written specification, with the claims and the drawings.

DETAILED DESCRIPTION OF THE PREFERRED EMBODIMENTS

Figure 1:
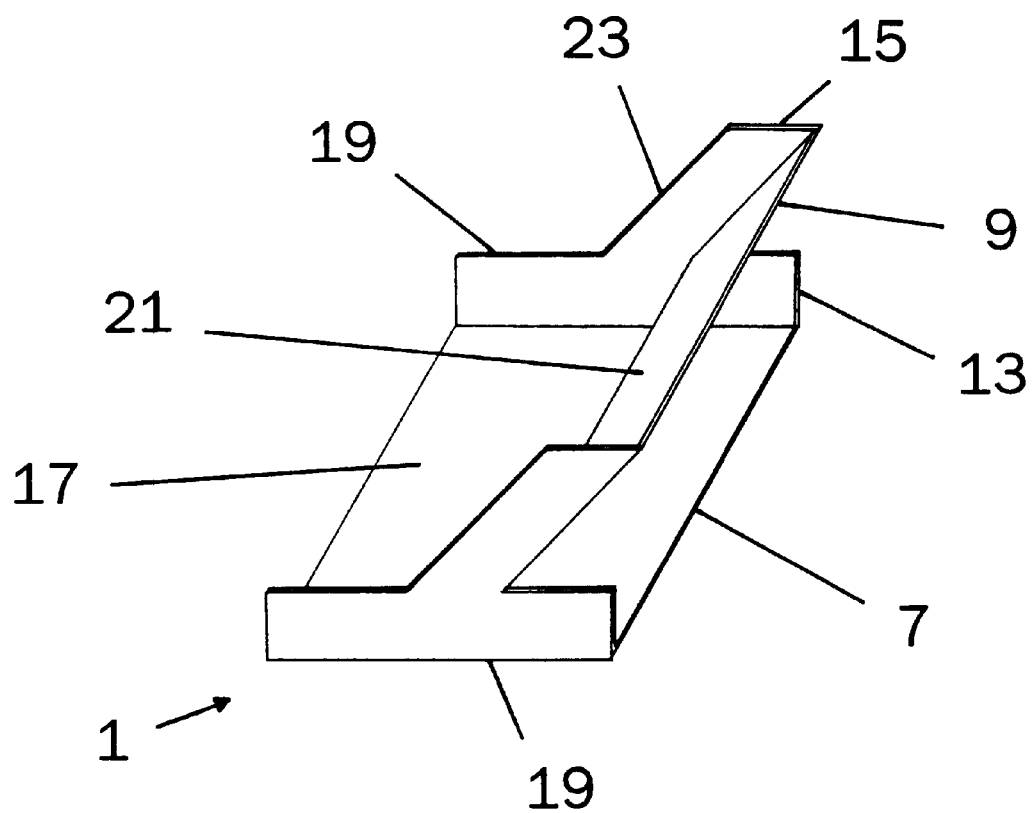
FIG. 1 shows a front perspective of the blood smearing cassette.
Figure 2:
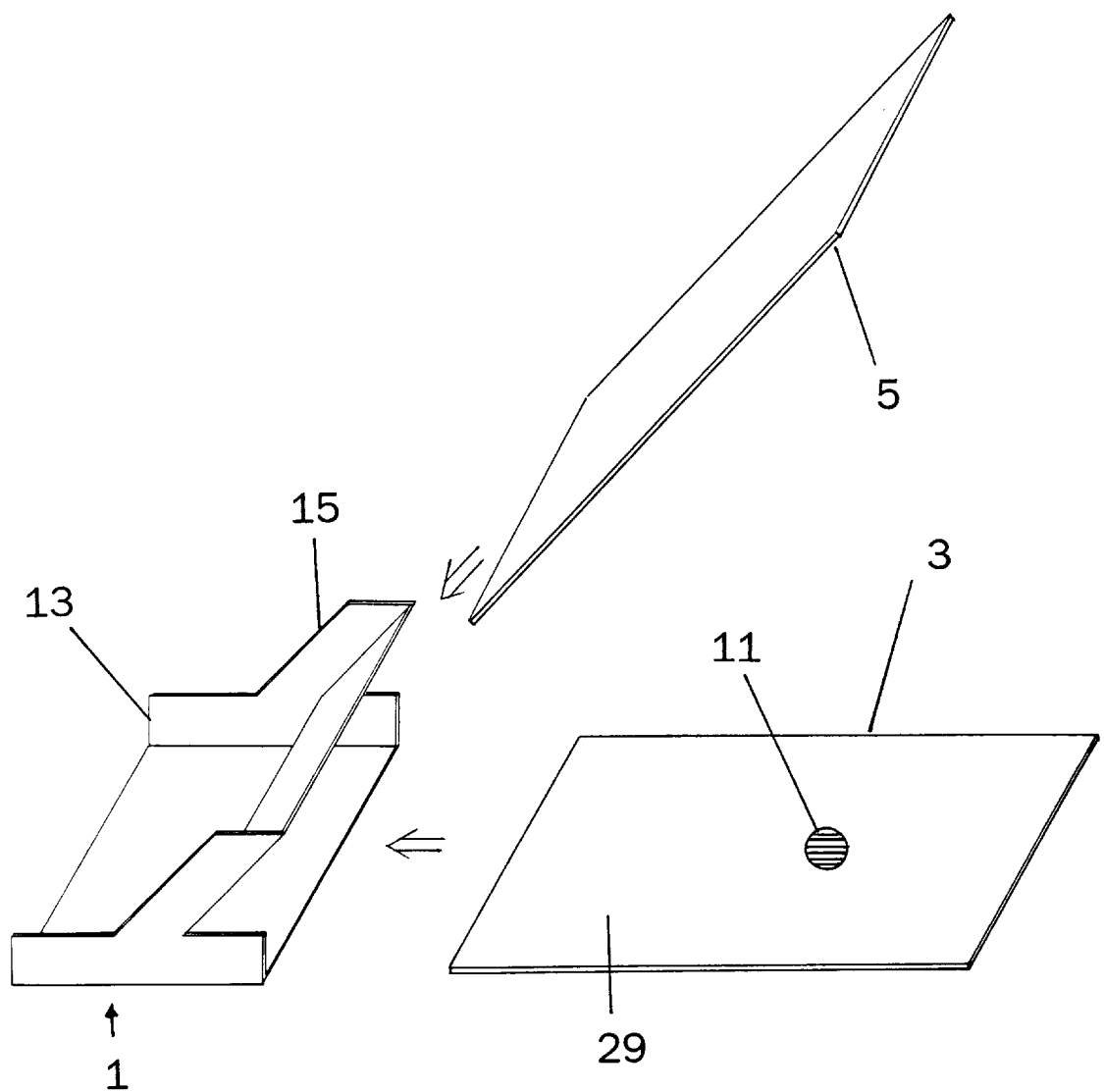
FIG. 2 is a front perspective of the blood smearing cassette receiving the insertion of the spreader slide and the smear slide.

As shown in FIGS. 1 and 2, the cassette 1 holds two slides, a smear slide 3 and a spreader slide 5, at specific angles to each other allowing relatively untrained personnel to make consistent and proper blood smears. The cassette 1 is comprised of two slide receivers 13 and 15 attached at a specified angle to each other. The smear slide receiver 13 consists of a base 17 with generally parallel walls 19 for holding a smear slide 3. Walls 19 may generally be perpendicular to base 17. The spreader slide receiver 15 consists of a base 21 with generally parallel walls 23 for holding a spreader slide 5. Walls 23 may generally be perpendicular to the base 21.

To use the cassette, the operator slips the smear slide 3 into the opening 7 of the smear slide receiver 13 that positions the smear slide horizontally. The spreader slide 5 is slipped into the opening 9 at the top of the spreader slide receiver 15. The spreader slide 5 drops onto the middle of the smear slide 3 by gravity. The spreader slide is held angularly with respect to the smear slide. Preferred angles are approximately between 30–40°. A small amount of blood 11 is placed on an upper surface 29 of the smear slide 3.

Figure 3:
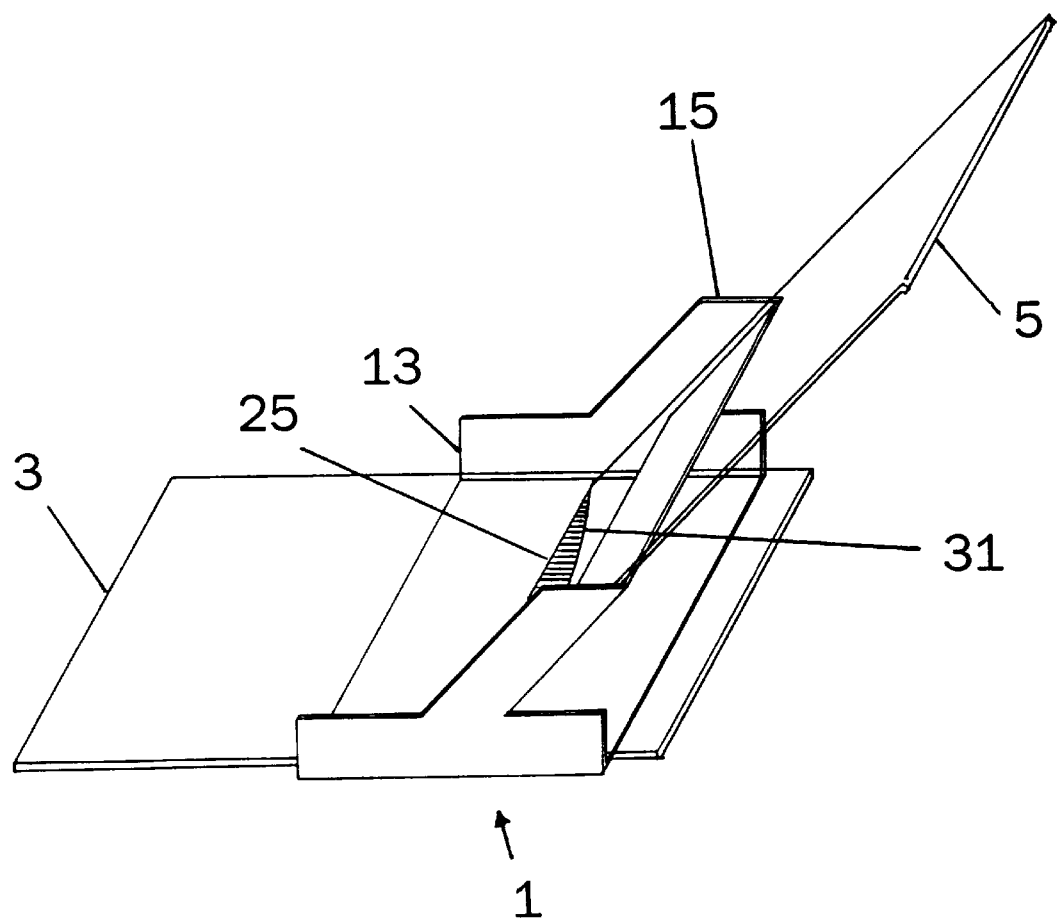
FIG. 3 is a front perspective of the blood smearing cassette with the spreading slide in contact with the blood on the smear slide.

FIG. 3 shows the horizontal smear slide 3 inserted in the cassette 1 and pulled up until the drop of blood just touches the spreader slide 15. The blood 31 is allowed to spread across the bottom 25 of the spreader slide 5.

Figure 4:
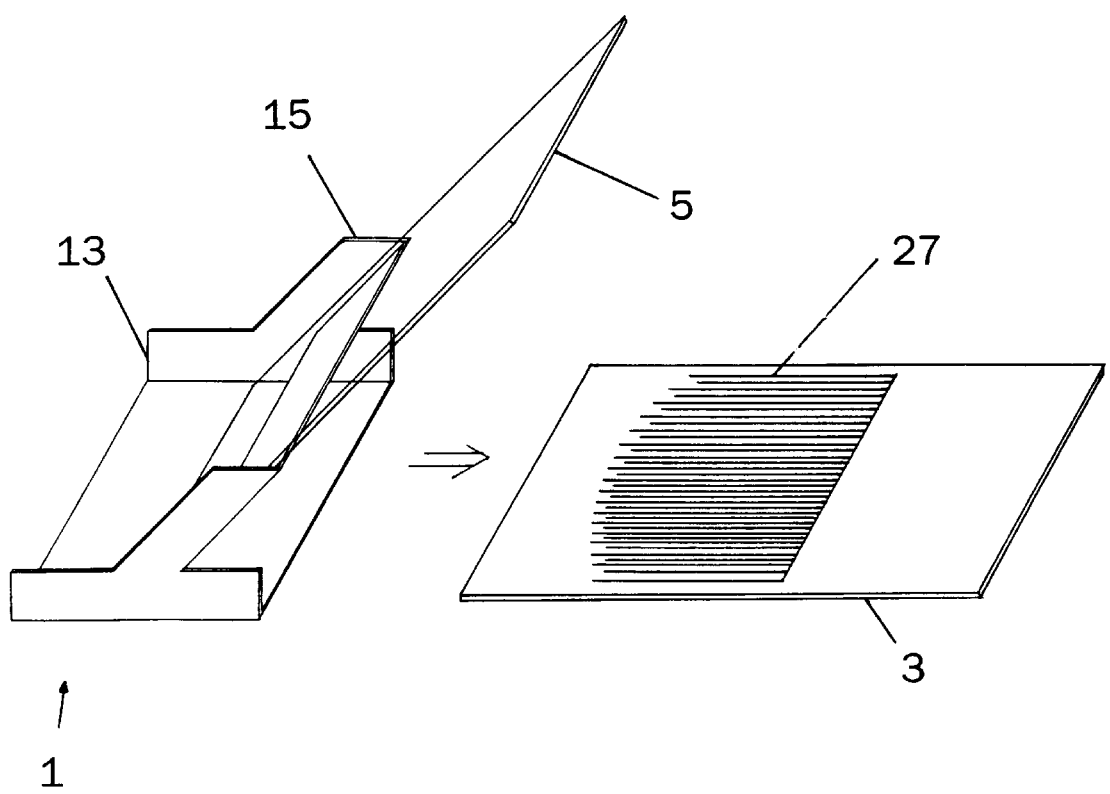
FIG. 4 is a front perspective of the prepared blood smear slide removed from the blood smearing cassette.

As shown in FIG. 4, the smear slide 3 is then pulled out of the smear slide receiver, leaving a thin film of blood 27 on the smear slide 3. The length and thickness of the film is controlled by pulling the smear slide 3 at different speeds and/or angles.

A preferred cassette is unitary with the slide receivers being formed together. The cassette being formed together. The cassette may be of any material. Preferred materials include polymers, such as, but not limited to, plastic.

Figure 5:
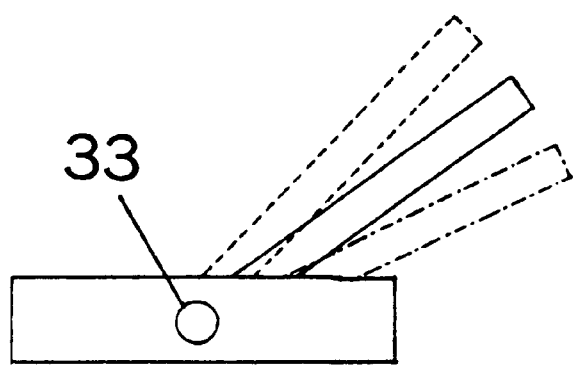
FIG. 5 is a front elevation of the blood smearing cassette with a pivotable connector.
Figure 6:
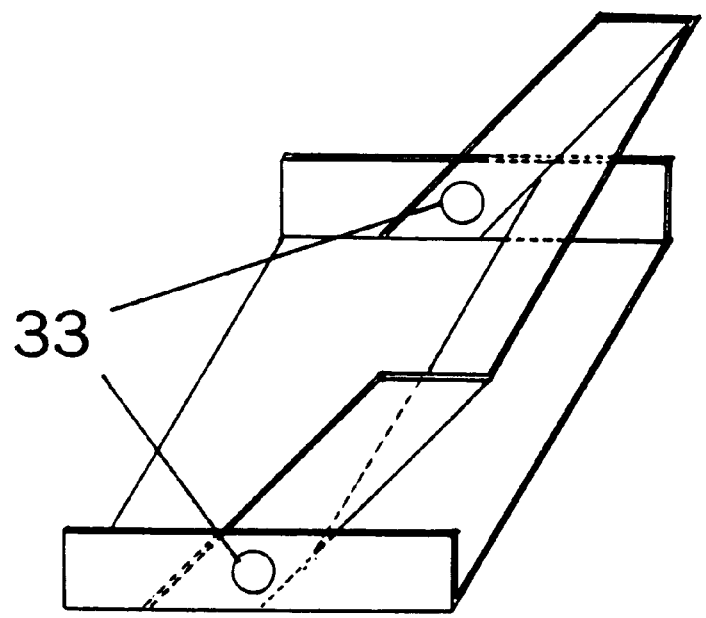
FIG. 6 is a front perspective of the blood smearing cassette with integrally molded living hinges.

In another preferred embodiment, a mechanism is added that allows for adjustment of the angle between the spreader slide and the smear slide. The mechanism may be a connector 31 for pivotally connecting the slide receivers, as shown in FIG. 5. Another preferred embodiment is a living hinge 33 in a unitarily molded or formed cassette, as shown in FIG. 6. The thicker the blood sample, the lower the angle that the spreader slide must be positioned in relation to the smear slide. The more liquid the blood sample, the higher the angle that the spreader slide must be positioned in relation to the smear slide. Different angles permit control of the film length and thickness according to sample viscosity (i.e., anemia vs. polycythemia).

While the invention has been described with reference to specific embodiments, modifications and variations of the invention may be constructed without departing from the scope of the invention, which is defined in the following claims.

I claim:

1. A blood smearing cassette apparatus comprising
a smear slide receiver having a planar smear slide receiver base for supporting a smear slide, and
a spreader slide receiver having a planar spreader slide base for supporting a rigid spreader slide, said spreader slide receiver base having a bottom end,
wherein the bottom end of the spreader slide receiver base is connected to the smear slide receiver so as to hold the spreader slide at an angle to the smear slide.

2. The apparatus of claim 1, further comprising a smear slide insertable into the smear slide receiver for holding a blood sample and a spreader slide insertable into the spreader slide receiver for smearing the blood sample on the smear slide.

3. The apparatus of claim 1, wherein the smear slide receiver is of a plastic material.

4. The apparatus of claim 1, wherein the spreader slide receiver is of a plastic material.

5. The apparatus of claim 1, further comprising a connector pivotally connecting a side of the spreader slide receiver to a side wall of the smear slide receiver for permitting pivoting in a predetermined range of angles between the smear slide receiver and the spreader slide receiver.

6. The apparatus of claim 5, wherein the predetermined range of angles consists of a range of about 30–40 degrees.

7. The apparatus of claim 1, further comprising at least one connector for connecting a side of the spreader slide receiver and a side wall of the smear slide receiver.

8. The apparatus of claim 7, wherein the at least one connector is provided for angularly adjusting the smear slide receiver on the spreader slide receiver.

9. The apparatus of claim 1, wherein the smear slide-receiver has wherein at least one side wall is perpendicular to the base for holding a smear slide.

10. The apparatus of claim 1, wherein the spreader slide receiver has at least one wall perpendicular to the base for holding a spreader slide.

11. The apparatus of claim 1, wherein the smear slide receiver has opposite walls perpendicular to the base for holding a smear slide.

12. The apparatus of claim 1, wherein the spreader slide receiver has opposite walls perpendicular to the base for holding a spreader slide.

13. A blood smearing cassette apparatus comprising a smear slide receiver having a planar smear slide for supporting a smear slide receiver base, a spreader slide receiver having a planar spreader slide receiver base for supporting a rigid spreader slide, said spreader slide receiver base having a bottom end, the bottom end of the spreader slide receiver being connected to the smear slide receiver at an angle, a smear slide insertable into the smear slide receiver for holding a blood sample, a spreader slide insertable into the rigid spreader slide receiver for smearing the blood sample on the smear slide, and at least one connector for connecting the spreader slide receiver and the smear slide receiver.

14. The apparatus of claim 13, wherein the smear slide receiver is of a plastic material.

15. The apparatus of claim 13, wherein the spreader slide receiver is of a plastic material.

16. The apparatus of claim 13, wherein the at least one connector is provided for angularly adjusting the smear slide receiver on the spreader slide receiver.

17. The apparatus of claim 13, wherein the smear slide receiver has at least one wall perpendicular to the base for holding a smear slide.

18. The apparatus of claim 13, wherein the spreader slide receiver has at least one wall perpendicular to the base for holding a spreader slide.

19. A blood smearing cassette apparatus comprising a smear slide receiver having a planar smear slide receiver base, for supporting a smear slide, a spreader slide receiver having a planar spreader slide receiver base, supporting a rigid spreader slide, said spreader slide receiver base having a bottom end, the bottom end of the spreader slide receiver being connected to the smear slide receiver, at an angle wherein the spreader slide receiver and the smear slide receiver are a unitary structure.

20. The apparatus of claim 19, further comprising a smear slide insertable into the smear slide receiver for holding a blood sample and a rigid spreader slide insertable into the spreader slide receiver for smearing the blood sample on the smear slide.

21. The apparatus of claim 19, wherein the cassette is of a plastic material.

22. The apparatus of claim 19, wherein the spreader slide receiver and the smear slide receiver are adjustably connected at an angle by a connector for adjusting the angle in a predetermined range of angles between the smear slide receiver and the spreader slide receiver.

23. The apparatus of claim 22, wherein the predetermined range of angles consists of a range of about 30–40 degrees.

24. The apparatus of claim 19, further comprising at least one connector that is unitarily formed with the smear slide receiver and the spreader slide receiver for connecting the spreader slide receiver and the smear slide receiver.

25. The apparatus of claim 24, wherein the at least one connector is provided for angularly adjusting the smear slide receiver on the spreader slide receiver.

26. The apparatus of claim 19, wherein the smear slide receiver has at least one wall perpendicular to the base for holding a smear slide.

27. The apparatus of claim 19, wherein the spreader slide receiver has at least one wall perpendicular to the base for holding a spreader slide.

28. The apparatus of claim 19, wherein the smear slide receiver has opposite walls perpendicular to the base for holding a smear slide.

29. The apparatus of claim 19, wherein the spreader slide receiver has opposite walls perpendicular to the base for holding a spreader slide.

30. A method for blood smearing comprising providing a smear slide receiver having a planar smear slide receiver base for supporting a smear slide, providing a spreader slide receiver having a planar spreader slide base for supporting a rigid spreader slide, said spreader slide receiver base having a bottom end, connecting the bottom end of the spreader slide receiver to the smear slide receiver so as to hold the spreader slide at an angle to the smear slide, mounting a smear slide in the smear slide receiver, mounting a rigid spreader slide in the spreader slide receiver, placing a blood sample on the smear slide, moving the smear slide with the blood sample under the spreader slide and smearing the blood sample on the smear slide with the spreader slide.

31. The method of claim 30, wherein connecting the smear slide receiver to the spreader slide receiver comprises providing an angular connection between the smear slide receiver and the spreader slide receiver, wherein an angle between the smear slide receiver and spreader slide receiver is in a range of about 30–40 degrees.

32. The method of claim 30, wherein connecting the smear slide receiver to the spreader slide receiver comprises providing at least one connector between the side wall of the smear slide receiver and the side of the spreader slide receiver.

33. The method of claim 32, wherein providing the at least one connector further comprises providing a connector for angularly adjusting the angle between the smear slide receiver and the spreader slide receiver.

34. The method of claim 30, further comprising positioning the inserted spreader slide on the smear slide receiver by gravity.

* * * * *